US011365427B2

(12) United States Patent
De Visser et al.

(10) Patent No.: US 11,365,427 B2
(45) Date of Patent: Jun. 21, 2022

(54) *SPINACIA OLERACEAE* PLANT RESISTANT TO *ALBUGO OCCIDENTALIS* AND *PERONOSPORA FARINOSA*

(71) Applicant: Pop Vriend Research B.V., Andijk (NL)

(72) Inventors: Jan De Visser, Andijk (NL); Johannes Marinus Rijk, Ens (NL); Johannes Simon Groenendijk, Wageningen (NL)

(73) Assignee: POP VRIEND SEEDS BV, Andijk (NL)

( * ) Notice: Subject to any disclaimer, the term of this patent is extended or adjusted under 35 U.S.C. 154(b) by 0 days.

(21) Appl. No.: 17/061,318

(22) Filed: Oct. 1, 2020

(65) Prior Publication Data
US 2021/0095306 A1   Apr. 1, 2021

Related U.S. Application Data

(60) Provisional application No. 62/909,110, filed on Oct. 1, 2019.

(51) Int. Cl.
| C12N 15/82 | (2006.01) |
| C12Q 1/6895 | (2018.01) |
| A01H 6/02 | (2018.01) |

(52) U.S. Cl.
CPC ....... C12N 15/8279 (2013.01); C12Q 1/6895 (2013.01); *C12Q 2600/13* (2013.01)

(58) Field of Classification Search
None
See application file for complete search history.

(56) References Cited

PUBLICATIONS

Brandenberger et al., 1994, Characterization of Resistance of Spinach to White Rust (*Albugo occidentalis*) and Downy Mildew (*Peronospora farinosa* f sp. *spinaciae*), Phytopathology 84: 431-437.*
Larkin et al., 1981, Somaclonal Variation—a Novel Source of Variability from Cell Cultures for Plant Improvement, Theor. Appl. Genet. 60: 197-214.*
•Awika et al., 2019, Minor alleles are associated with white rust (*Albugo occidentalis*) susceptibility in spinach (*Spinacia oleracea*), Horticulture Research 6:129, pp. 1-15.*
Correll et al., Update on downy mildew and white rust on spinach in the United States, 2003, Eucarpia Leafy Vegetables 2003, eds. Th.J.L. van Hintum, A. Lebeda, D. Pink, J.W. Schut, pp. 49-54.*
Correll et al., "Update on downy mildew and white rust on spinach in the United States", Eucarpia Leafy Vegetables, pp. 49-54 2003.
Hibberd et al., "Allelism Tests of Three Dominant Genes for Hypersensitive Resistance to Bacterial Spot of Pepper", Phytopathology, vol. 77, No. 9, pp. 1304-1307, Feb. 5, 1987.

* cited by examiner

*Primary Examiner* — Bratislav Stankovic
(74) *Attorney, Agent, or Firm* — McKee, Voorhees & Sease, PLC

(57) ABSTRACT

The present disclosure relates to the field of plant breeding and, more specifically, to the development of white rust (*Albugo occidentalis*) resistant and downy mildew (*Peronospora farinosa* f. sp. spinaceae) resistant spinach plants having elite agronomic traits. The resistance to white rust is conferred by one or more alleles that co-segregate with at least one molecular marker selected from the group of SEQ ID No. 1-10. The resistance to downy mildew is conferred by an allele that co-segregates with at least one molecular marker selected from the group of SEQ ID No. 11-13. The disclosure relates further to the use of the molecular markers.

24 Claims, No Drawings
Specification includes a Sequence Listing.

SPINACIA OLERACEAE PLANT RESISTANT TO ALBUGO OCCIDENTALIS AND PERONOSPORA FARINOSA

CROSS-REFERENCE TO RELATED APPLICATION

This application claims the benefit of U.S. Provisional Application No. 62/909,110, filed Oct. 1, 2019, which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 781982001000SEQLIST.txt, date recorded: Sep. 24, 2020, size: 7 KB).

FIELD

The present disclosure relates to the field of plant breeding and, more specifically, to the development of white rust (*Albugo occidentalis*) resistant and downy mildew (*Peronospora farinosa* f sp. spinaceae) resistant spinach plants having elite agronomic traits.

BACKGROUND

Crop improvement, the engineering of plants for the benefit of humanity, is as old as agriculture itself. The enhancement of plants aims to obtain plant varieties that are superior to those available in the market, either in the production of seeds, biomass, in resistance to pests and diseases, or other traits of interests.

Spinach (*Spinacia oleracea* L.) has become an increasingly important vegetable crop in many parts of the world. In addition to its economic importance, spinach is one of the healthiest vegetables in the human diet due to its high concentration of nutrients and health-promoting compounds. Significant changes in production practices, particularly in the U.S. and E.U., have occurred as a result of increased product demand. These changes likely increased the incidence and severity of white rust and downy mildew caused by the obligate-biotrophic oomycete pathogens *Albugo occidentalis* (Ao) and *Peronospora farinosa* f sp. spinaceae (Pfs), respectively. Downy mildew is a major production constraint virtually everywhere the crop is grown, whereas white rust is limited, for now, to the U.S., Greece, Mexico, Turkey, and Italy. Both pathogens can cause substantial yield losses and reduce quality of both fresh and processed spinach.

Pest management involves preventive and curative measures including chemical treatment. Plowing or disking diseased plants and plant parts results in rapid decomposition of infected tissues and helps to significantly reduce future white rust infection. Crop rotation with non-amaranth host plants is also effective. Weed control and other sanitary methods are necessary too.

A number of surfactants and natural products have been effective at reducing white rust and downy mildew severity (Correl et al. (2003)). Although fungicides minimize losses, the use of resistant or tolerant cultivars is the best alternative for controlling the disease, in order to reduce costs, facilitate management and help in environmental conservation. Therefore, good genetic resistance of the crop is important for its protection against the disease.

Because single-gene resistance to white rust is not available for spinach and only a few commercially available cultivars have quantitative resistance to white rust, the development of spinach cultivars with increased levels of white rust resistance will continue to make this type of resistance an effective management tool.

There remains a need in the art to provide plants which are less or not susceptible to white rust and various known downy mildew races. This requires the development of improved cultivars to increase spinach production. The present disclosure aims to resolve at least some of the problems and disadvantages mentioned above.

BRIEF SUMMARY

The present disclosure and embodiments thereof serve to provide a solution to one or more of the above-mentioned disadvantages. To this end, the present disclosure relates to a cultivated spinach (*Spinacia oleracea* L.) plant. In one aspect, the cultivated spinach plant of the current disclosure is resistant to white rust caused by the plant pathogen *Albugo occidentalis* (Ao). Said resistance to Ao is conferred by the presence of one or more resistance alleles. These resistance alleles provide an improved quantitative resistance to Ao in comparison to cultivars without these resistance alleles, and therefore without resistance to Ao.

In one aspect, the cultivated spinach plant is resistant to white rust caused by the plant pathogen Ao, characterized in that said resistance is provided by one or more resistance alleles conferring resistance to said plant pathogen, and wherein said alleles co-segregate with at least one molecular marker selected from the group of SEQ ID No. 1 including a T to C SNP at nucleotide 101, SEQ ID No. 2 including a T to A SNP at nucleotide 101, SEQ ID No. 3 including an A to G SNP at nucleotide 101, SEQ ID No. 4 including a G to A SNP at nucleotide 101, SEQ ID No. 5 including a T to C SNP at nucleotide 101 and a G to A SNP at nucleotide 158, SEQ ID No. 6 including a C to A SNP at nucleotide 101, SEQ ID No. 7 including a G to T SNP at nucleotide 101, SEQ ID No. 8 including a C to T SNP at nucleotide 101, SEQ ID No. 9 including a C to T SNP at nucleotide 101, or SEQ ID No. 10 including an A to G SNP at nucleotide 101. In certain embodiments, the improved cultivated spinach plant is further resistant to downy mildew caused by the plant pathogen *Peronospora farinosa* f. sp. *spinaciae* (Pfs), wherein the resistance to Pfs is to at least Pfs races 1 to 15 and race 17, and wherein said resistance is provided by a fourth allele conferring resistance to said plant pathogen. In some embodiments, said fourth resistance allele co-segregates with at least one molecular marker selected from the group of SEQ ID No. 11 including an A to G SNP at nucleotide 101, SEQ ID No. 12 including a G to A SNP at nucleotide 101, or SEQ ID No. 13 including a T to C SNP at nucleotide 101.

In a preferred embodiment, the cultivated spinach plant of the current disclosure is resistant to white rust (Ao) and downy mildew (Pfs) as a result of the presence of specific resistance alleles. In one embodiment, the Ao resistance is provided by a first resistance allele located on chromosome 1 of said plant, wherein said allele co-segregates with at least one molecular marker selected from the group of SEQ ID No. 1 including the T to C SNP at nucleotide 101, SEQ ID No. 2 including the T to A SNP at nucleotide 101, or SEQ ID No. 3 including the A to G SNP at nucleotide 101. In another embodiment, the Ao resistance is provided by a second resistance allele located on chromosome 2 of said plant, wherein said allele co-segregates with at least one molecular marker selected from the group of SEQ ID No. 4 including the G to A SNP at nucleotide 101, SEQ ID No. 5 including the T to C SNP at nucleotide 101 and the G to A SNP at nucleotide 158, or SEQ ID No. 6 including the C to A SNP at nucleotide 101. In yet another embodiment, the Ao resistance is provided by a third resistance allele located on chromosome 3 of said plant, wherein said allele co-segregates with at least one molecular marker selected from the group of SEQ ID No. 7 including the G to T SNP at nucleotide 101, SEQ ID No. 8 including the C to T SNP at nucleotide 101, SEQ ID No. 9 including the C to T SNP at nucleotide 101, or SEQ ID No. 10 including the A to G SNP at nucleotide 101. In an additional embodiment, the Ao resistance is conferred by two or more resistance alleles including the first resistance allele, the second resistance allele, and the third resistance allele. In some embodiments, the first resistance allele, the second resistance allele, and the third resistance allele are present in the plant in homozygous state. In a further embodiment, the resistance to Pfs is provided by a fourth resistance allele conferring resistance to Pfs, characterized in that said fourth resistance allele is located on chromosome 3, and that said fourth resistance allele co-segregates with at least one molecular marker selected from the group of SEQ ID No. 11 including the A to G SNP at nucleotide 101, SEQ ID No. 12 including the G to A SNP at nucleotide 101, or SEQ ID No. 13 including the T to C SNP at nucleotide 101. In some embodiments, the fourth resistance allele is present in the plant in homozygous state.

In further aspects, the present disclosure relates to cell or tissue material, seed, progeny, and propagation material of the cultivated spinach plant of current disclosure, and use thereof. Propagating material derived from the cultivated spinach plant is selected from the group of stems, cuttings, petioles, hypocotyls, cotyledons, flowers, anthers, pollen, ovaries, roots, root tips, protoplasts, callus, microspores, stalks, ovules, shoots, seeds, embryos, embryo sacs, egg cells, cells, meristems, buds, or leaves, and said propagation material is capable of growing into a spinach plant according to any one of the above embodiments. In one embodiment, this disclosure is directed to progeny of a spinach plant according to any one of the above embodiments that has resistance to Ao, wherein said progeny retains the one or more resistance alleles which confer resistance to Ao. In a further embodiment, this disclosure is directed to progeny of a spinach plant according to any one of the above embodiments that has resistance to Ao and Pfs, wherein said progeny retains the one or more resistance alleles which confer resistance to Ao and Pfs. In another embodiment, this disclosure is directed to a tissue culture of a spinach plant according to any one of the above embodiments that has resistance to Ao, and the spinach plant regenerated from the tissue culture, wherein said regenerated plant retains the one or more resistance alleles which confers resistance to Ao. In an additional embodiment, this disclosure is directed to a tissue culture of a spinach plant according to any one of the above embodiments that has resistance to Ao and Pfs, and the spinach plant regenerated from the tissue culture, wherein said regenerated plant retains the resistance alleles which confer resistance to Ao and Pfs. In some embodiments, which may be combined with any of the preceding embodiments, the cultivated spinach plant was produced by growing seed of inbred spinach variety designated as 'X17-003-104-8', representative sample of seed having been deposited under NCIMB Accession Number 43477.

In another aspect, the present disclosure relates to a seed of inbred spinach variety designated as 'X17-003-104-8', representative sample of seed having been deposited under NCIMB Accession Number 43477.

In a further aspect, this disclosure is directed to a method of generating a cultivated spinach plant including resistance to Ao or Ao and Pfs, including the steps: (a) crossing the spinach plant produced by growing the seeds deposited under NCIMB Accession Number 43477 with itself or with a second spinach plant; and (b) selecting an F1 progeny plant including resistance to Ao or an F1 progeny plant including resistance to Ao and Pfs. In some embodiments, the method further includes the steps: (c) crossing the F1 progeny plant with a second spinach plant to produce backcross progeny plants; and (d) selecting a backcross progeny plant including resistance to Ao or a backcross progeny plant including resistance to Ao and Pfs.

In additional embodiments, the present disclosure relates to methods of identifying the resistant spinach plant according to any one of the above embodiments that has resistance to Ao, including the identification of one or more molecular markers selected from the group of the resistant alleles of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, or SEQ ID No. 10. In further embodiments, the present disclosure relates to methods of identifying the resistant spinach plant according to any one of the above embodiments that has resistance to Ao and Pfs, including the identification of one or more molecular markers selected from the group of the resistant alleles of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, or SEQ ID No. 10, SEQ ID No. 11, SEQ ID No. 12, or SEQ ID No. 13. In some embodiments, the present disclosure relates to a method of monitoring introgression of Ao and/or Pfs resistance alleles in spinach plants, and/or developing other markers co-segregating with Ao and/or Pfs resistance alleles.

Definitions

Unless otherwise defined, all terms used in disclosing the disclosure, including technical and scientific terms, have the meaning as commonly understood by one of ordinary skill in the art to which this disclosure belongs. By means of further guidance, term definitions are included to better appreciate the teaching of the present disclosure.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosure. However, it is to be understood that the value to which the modifier "about" refers is itself also specifically disclosed.

"Comprise", "include", and "contain" and grammatical variants thereof are inclusive or open-ended terms that specifies the presence of what follows, e.g., component and do not exclude or preclude the presence of additional, non-recited components, features, element, members, steps, known in the art or disclosed therein.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the disclosure described herein are capable of operation in other sequences than described or illustrated herein.

The recitation of numerical ranges by endpoints includes all numbers and fractions subsumed within that range, as well as the recited endpoints.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any $\geq 3$, $\geq 4$, $\geq 5$, $\geq 6$ or $\geq 7$ etc. of said members, and up to all said members.

The term "spinach", "cultivated spinach", "cultivated spinach plant", or "spinach plant" is understood within the scope of the disclosure to refer to plants of the species Spinacia oleracea L., seeds from which the plants can be grown, or propagation material or parts of such plants. These are no longer in the natural state but have been developed by human intervention and for human use and/or consumption.

As used herein the term "genotype" refers to the genetic constitution of a cell or organism. An individual's genotype for a set of markers includes the specific alleles, for one or more genetic marker loci, present in the individual's haplotype. As is known in the art, a genotype can relate to a single locus or to multiple loci, whether the loci are related or unrelated and/or are linked or unlinked.

"Phenotype" is understood within the scope of the disclosure to refer to a distinguishable characteristic(s) of a genetically controlled trait. For example, the cultivated spinach plant of current disclosure has a savoy, compact fast-growing, very-dark colored, monoecious phenotype.

As used herein, the term "trait" or "phenotypic trait" refers to the appearance or other detectable characteristic of an individual, resulting from the interaction of its genome, transcriptome, proteome and/or metabolome with the environment. A trait may be inherited in a dominant or recessive manner, or in a partial or incomplete-dominant manner. A trait may be monogenic (i.e. determined by a single locus) or polygenic (i.e. determined by more than one locus) or may also result from the mutual interaction among genes or interaction of one or more genes with the environment. A dominant trait results in a complete phenotypic manifestation at heterozygous or homozygous state; a recessive trait manifests itself only when present at homozygous state.

An "allele" is understood within the scope of the disclosure to refer to any of one or more alternative or variant forms of various genetic units identical or associated with different forms of a gene or of any kind of identifiable genetic element, all of which alleles relate to at least one trait or characteristic. In a diploid cell, the two alleles of a given gene occupy corresponding loci on a pair of homologous chromosomes and are, therefore, alternative in inheritance. Such alternative or variant forms may be the result of single nucleotide polymorphism, insertions, inversions, translocations or deletions, or the consequence of gene regulation caused by, for example, by chemical or structural modification, transcription regulation or post-translational modification/regulation. Alleles determine distinct traits that can be passed on from parents to offspring. An allele associated with an resistance gene may comprise alternative or variant forms of various genetic units including those that are identical or associated with a single gene or multiple genes or their products or even a gene disrupting or controlled by a genetic factor contributing to the phenotype represented by the locus.

As used herein, "resistance allele" includes the polymorphic allele associated with resistance to the disease of current disclosure.

"Locus" is understood within the scope of the disclosure to refer to a region on a chromosome. The locus is specified using the cytogenetic banding nomenclature known in the art.

The term "homologous chromosomes" as used herein is to be understood as chromosome pairs, one from each parent, that are similar in length, gene position, and centromere location. The position of the genes on each homologous chromosome is the same. However, the genes may contain different alleles.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes. Homozygosity is defined as absence of segregation after selfing of an individual plant or, if crossed, absence of segregation in F1.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

The term "genetic linkage" is understood to refer to an association of characters in inheritance due to location of genes in proximity on the same chromosome, measured by percent recombination between loci (centi-Morgan, cM).

The term "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "Co-segregation" also refers to the presence of two or more traits within a single plant of which at least one is known to be genetic and which cannot be readily explained by chance.

As used herein, the term "marker", "molecular marker" or "genetic marker" refer to an alternative or variant form of a genetic unit, when used as a marker to locate genetic loci containing alleles on a chromosome that contribute to variability of phenotypic traits. Markers include, for example, single nucleotide variations (SNVs), single nucleotide polymorphisms (SNPs), simple sequence repeats (SSRs), microsatellite markers, restriction fragment length polymorphisms (RFLPs), random amplified polymorphic DNAs (RAPDs), cleaved amplified polymorphic sequence (CAPS) markers, diversity arrays technology (DART) markers, and amplified fragment length polymorphism (AFLPs), among many other examples. Molecular markers can, for example, be used to locate genetic loci containing alleles on a chromosome that contribute to variability of phenotypic traits. A marker can be physically located in a position on a chromosome that is within or outside of the genetic locus with which it is associated (i.e. intragenic or extragenic, respectively).

A "SNP marker" is a single nucleotide base difference between two DNA sequences or individuals. Single Nucleotide Polymorphisms (SNPs) can be categorized according to nucleotide substitutions either as transitions (C/T or G/A) or transversions (C/G, A/T, C/A or T/G). In practice, single base variants in cDNA (mRNA) are considered to be SNPs as are single base insertions and deletions (indels) in the genome. SNPs provide the simplest form of molecular markers as a single nucleotide base is the smallest unit of inheritance, and thus they can provide maximum markers. SNPs occur very commonly in plants. Typically, SNP frequencies are in a range of one SNP every 100 to 300 bp in plants. SNPs may present within the coding sequences of genes, the non-coding regions of genes or in the intergenic regions between genes at different frequencies in different chromosome regions.

As used herein the term "breeding" and grammatical variants thereof, refer to any process that generates a progeny. Breeding can be sexual or asexual, or any combination thereof. Exemplary non-limiting types of breeding include crossings, settings, doubled haploid derivative generation, and combinations thereof.

"Backcrossing" is understood within the scope of the disclosure to refer to a process in which a hybrid progeny is repeatedly crossed back to one of the parents. Different recurrent parents may be used in subsequent backcrosses.

As used herein, the phrases "sexually crossed" and "sexual reproduction" in the context of the presently disclosed subject matter refers to the fusion of gametes to produce progeny (e.g., by fertilization, such as to produce seed by pollination in plants).

An "asexual cross" or "cross-fertilization" is to be understood as fertilization of one individual by another (e.g., cross-pollination in plants).

The term "selfing" refers to the production of seed by self-fertilization or self-pollination, i.e. pollen and ovule are from the same plant.

As used herein, the terms "hybrid", "hybrid plant," and "hybrid progeny" refers to an individual produced from genetically different or unlike parents (e.g., a genetically heterozygous or mostly heterozygous individual).

As used herein, the phrase "single cross F1 hybrid" refers to an F1 hybrid produced from a cross between two inbred lines.

As used herein, the phrase "inbred line" refers to a genetically homozygous or nearly homozygous population. An inbred line, for example, can be derived through several cycles of brother/sister breeding or of selfing. An "inbred", "inbred individual", or "inbred progeny" is an individual sampled from an inbred line.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the F1, the F2, or any subsequent generation.

As used herein, the terms "introgression", "introgressed" and "introgressing" refer to the process whereby genes, alleles or haplotype of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

"Polymorphism" is understood within the scope of the disclosure to refer to the presence in a population of two or more different forms of a gene, genetic marker, or inherited trait or a gene product obtainable, for example, through alternative splicing, DNA methylation, etc.

"Selective breeding" is understood within the scope of the disclosure to refer to a program of breeding that uses plants that possess or display desirable traits as parents.

As used herein, the term "population" means a genetically homogeneous or heterogeneous collection of plants sharing a common genetic derivation.

"Ao" or "*Albugo*" or "white rust" refers to the pathogen *Albugo occidentalis*.

"Pfs" or "*Peronospora farinosa*" or "downy mildew" refers to races of the pathogen *Peronospora farinosa* f sp. *spinaciae*. Pfs 1-17 refer to the officially recognized races, which can be differentiated on the differential hosts of spinach and which can be obtained from the Naktuinbouw, P.O. Box 40, 2370 AA Roelofarendsveen, The Netherlands, or via references provided by the ISF (International Seed Federation).

As used herein, the term "full resistance" is referred to as complete failure of the pathogen to develop after infection, and may either be the result of failure of the pathogen to enter the cell (no initial infection) or may be the result of failure of the pathogen to multiply in the cell and infect subsequent cells (no subliminal infection, no spread). The presence of full resistance may be determined by establishing the absence of pathogen protein or pathogen RNA in cells of the plant, as well as the absence of any disease symptoms in said plant, upon exposure of said plant to an infective dosage of pathogen (i.e. after 'infection'). Among breeders, this phenotype is often referred to as "immune".

"Immunity" as used herein thus refers to a form of resistance characterized by absence of pathogen replication even when the pathogen is actively transferred into cells by e.g., electroporation.

As used herein, the term "partial resistance" is referred to as reduced multiplication of the pathogen in the cell, as reduced (systemic) movement of the pathogen, and/or as reduced symptom development after infection. The presence of partial resistance may be determined by establishing the systemic presence of low concentration of pathogen protein or pathogen RNA in the plant and the presence of decreased or delayed disease-symptoms in said plant upon exposure of said plant to an infective dosage of pathogen. Protein concentration may be determined by using a quantitative detection method (e.g., an ELISA method or a quantitative reverse transcriptase-polymerase chain reaction (RT-PCR)). Among breeders, this phenotype is often referred to as "intermediate resistant."

The term "*Albugo* resistance", "resistant to *Albugo*", or similar terms as used herein refers to a cultivated spinach plant that highly restrict the growth and development of the specified plant pathogen under normal pathogen pressure when compared to susceptible counterparts. These plants may, however, exhibit some symptoms or damage under heavy pathogen pressure. The level of resistance to Ao exhibited by the cultivated spinach plant can be scored by known assays in the art.

As used herein, the phrase "susceptibility" refers to the inability of a plant to adequately restrict the growth and development of a specified plant pathogen, particularly of a plant pathogen Ao and/or a plant pathogen Pfs, particularly a spinach plant of *Spinacia oleracea* L.

All references cited in the present specification are hereby incorporated by reference in their entirety. In particular, the teachings of all references herein specifically referred to are incorporated by reference.

Unless otherwise defined, all terms used in disclosing the disclosure, including technical and scientific terms, have the meaning as commonly understood by one of ordinary skill in the art to which this disclosure belongs. By means of further guidance, definitions for the terms used in the description are included to better appreciate the teaching of the present disclosure. The terms or definitions used herein are provided solely to aid in the understanding of the disclosure.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

DETAILED DESCRIPTION

The present disclosure relates to plants resistant to Ao and to plants resistant to Ao and Pfs, in particular cultivated spinach (*Spinacia oleracea* L.) plants. The disclosure further relates to cell and tissue material, seeds, progeny and propagation material of said plants, and use thereof. The disclosure also relates to molecular markers and use thereof. These new genomic resources significantly augment white rust management. Furthermore, the resistance to said plant pathogens is combined with desirable agronomic traits in the cultivated spinach plant of the current disclosure.

Spinach (*Spinacia oleracea* L.), is a flowering plant of the genus *Spinacia* in subfamily Chenopodioideae of family Amaranthaceae in the order Caryophyllales. Spinach is a diploid organism with 2n=12 chromosomes and is related to chard (*Beta vulgaris* L. *Cicla* group), sugar beet (*B. vulgaris* L. *Altissima* group), and table beet (*B. vulgaris* L. *Crassa* group). As in many vegetable crops, breeding activities are mainly directed to quality characteristics and improvement of the resistance to pests and diseases. Leaf traits (amount, length, quality), surface texture (smooth, savoy or semi-savoy), petiole color (different shades of green vs. purple) and edge shape (serrate vs. entire), are important commercial traits of spinach. Further important commercial traits of spinach are resistance to pests or diseases, like white rust.

White rust of spinach is caused by the obligate-biotrophic oomycete pathogen Ao. Ao propagates sexually and asexually. The oospore, which is the result of karyogamy of two haploid gametes, can overwinter in the soil. In the spring the oospore produces zoospores which will encyst on the surface of spinach leaves, in the presence of water, and germinate. The asexual propagation of Ao occurs via the production of sporangia and sporangiophores. These sporangia disperse and form zoospores, which complete the asexual cycle by (re)infecting a new spinach leaf. Initial symptoms of infection include small chlorotic lesions on top of the leaves produced by white rust pustules on the underside of the leaf. Further development of the disease causes leaf yellowing and stunted growth ultimately resulting in plant death.

In a first aspect, the disclosure provides a cultivated spinach (*Spinacia oleracea* L.) plant, wherein said plant is resistant against white rust caused by the plant pathogen Ao, wherein said resistance is provided by one or more alleles conferring resistance to said plant pathogen, and wherein said alleles co-segregate with at least one molecular marker selected from the group of the resistant alleles of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, or SEQ ID No. 10. In some embodiments, the plant was produced by growing seed of inbred spinach variety designated as 'X17-003-104-8', representative sample of seed having been deposited under NCIMB Accession Number 43477.

Resistance to Ao is not a single gene immunity, but rather a polygenic and quantitative resistance. A person skilled in the art will appreciate that the cultivated spinach plant of current disclosure includes one or more alleles conferring resistance to Ao. The molecular makers co-segregating with said alleles contain a single nucleotide polymorphism in their sequence and are called SNP markers.

Of the classes of genetic markers, SNPs have characteristics which make them preferential to other genetic markers in detecting, selecting for, and introgressing disease resistance in spinach. SNPs are preferred because technologies are available for automated, high-throughput screening of SNP markers, which can decrease the time to select for and introgress disease resistance in spinach plants. Further, SNP markers are ideal because the likelihood that a particular SNP allele is derived from independent origins in the extant population of a particular species is very low. As such, SNP markers are useful for tracking and assisting introgression of disease resistance alleles, particularly in the case of disease resistance haplotypes.

In one embodiment, the Ao resistance in said cultivated spinach (*Spinacia oleracea* L.) of current disclosure is provided by a first resistance allele located on chromosome 1. The first resistance allele co-segregates with at least one molecular marker selected from the group of the resistant alleles of SEQ ID No. 1, SEQ ID No. 2, and/or SEQ ID No. 3. Preferably, the first resistance allele co-segregates with at least two molecular markers selected from the group of the resistant alleles of SEQ ID No. 1, SEQ ID No. 2, and/or SEQ ID No. 3. More preferably the first resistance allele co-segregates with the three resistant alleles of molecular markers SEQ ID No. 1, SEQ ID No. 2, and SEQ ID No. 3. In some embodiments, the first Ao resistance allele is present in the plant in homozygous state.

In a further embodiment, the Ao resistance in said cultivated spinach (*Spinacia oleracea* L.) of the current disclosure is provided by a second resistance allele located on chromosome 2. When aligned to the *Spinacia oleracea* UCD Spo v3.0 genome available on JGI Phytozome (https://phytozome-next.jgi.doe.gov), the second resistance allele is located on chromosome 4. The second resistance allele co-segregates with at least one molecular marker selected from the group of the resistant alleles of SEQ ID No. 4, SEQ ID No. 5, and/or SEQ ID No. 6. Preferably, the second resistance allele co-segregates with at least two molecular markers selected from the group of the resistant alleles of SEQ ID No. 4, SEQ ID No. 5, and/or SEQ ID No. 6. More preferably, the second resistance allele co-segregates with the three resistant alleles of the molecular markers SEQ ID No. 4, SEQ ID No. 5, and SEQ ID No. 6. In some embodiments, the second Ao resistance allele is present in the plant in homozygous state.

In another and further embodiment, the Ao resistance in said cultivated spinach (Spinacia oleracea L.) of the current disclosure is provided by a third resistance allele located on chromosome 3. The third resistance allele co-segregates with at least one molecular marker selected from the group of the resistant alleles of SEQ ID No. 7, SEQ ID No. 8, SEQ ID No. 9, and/or SEQ ID No. 10. Preferably, the third resistance allele co-segregates with at least two molecular markers selected from the group of the resistant alleles of SEQ ID No. 7, SEQ ID No. 8, SEQ ID No. 9, and/or SEQ ID No. 10. More preferably, the third resistance allele co-segregates with at least three molecular marker selected from the group of the resistant alleles of SEQ ID No. 7, SEQ ID No. 8, SEQ ID No. 9, and/or SEQ ID No. 10. Even more preferably, the third resistance allele co-segregates with the four resistant alleles of molecular markers SEQ ID No. 7, SEQ ID No. 8, SEQ ID No. 9, and SEQ ID No. 10. In some embodiments, the third Ao resistance allele is present in the plant in homozygous state.

In an additional embodiment, the Ao resistance of the cultivated spinach plant of the current disclosure is conferred by two or more resistance alleles, including the first resistance allele, the second resistance allele, and/or the third resistance allele. In some embodiments, the first resistance allele, the second resistance allele, and the third resistance allele are present in the plant in homozygous state.

In one embodiment, the disclosure relates to the cultivated spinach plant according to the current disclosure, wherein said molecular markers can be identified in a PCR reaction with a pair of PCR oligonucleotide primers. Design of suitable PCR primers is known to a person skilled in the art.

Various methods for identifying and obtaining cultivated spinach plants with resistance to Ao are provided herein. In one embodiment, a method of identifying a cultivated spinach plant including at least one allele associated with Ao resistance allele in a spinach plant includes: (a) genotyping at least one cultivated spinach plant with at least one molecular marker selected from the group of the resistant alleles of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, and/or SEQ ID No. 10, and (b) selecting at least one cultivated spinach plant including an allele of at least one of said markers associated with Ao resistance. In certain embodiments of the methods, the at least one spinach plant genotyped in step (a) and/or the at least one spinach plant selected in step (b) is a spinach plant from a population generated by a cross. In embodiments where the population is generated by a cross, the cross can be effected by mechanical emasculation, chemical sterilization, or genetic sterilization of a pollen acceptor. In certain embodiments of the methods, genotyping is effected in step (a) by determining the allelic state of at least one of said spinach genomic DNA markers. In certain embodiments of the methods, the selected one or more spinach plants can exhibit at least partial resistance to Ao or at least substantial resistance to Ao. In certain embodiments of the methods, the population can be generated by a cross of at least one Ao resistant spinach plant with at least one Ao sensitive spinach plant. In certain embodiments of the methods, the population can be a segregating population. In certain embodiments of the methods, the cross can be a back cross of at least one Ao resistant spinach plant with at least one Ao sensitive spinach plant to introgress Ao resistance into a spinach germplasm. Similar methods may be applied for identifying and obtaining cultivated spinach plants with resistance to Ao and Pfs.

Also provided herein are cultivated spinach plants obtained by any of the aforementioned methods of identifying cultivated spinach plants that comprise alleles associated with Ao resistance. In certain embodiments, the cultivated spinach plant obtained by any of these aforementioned methods can include at least one allele of a nucleic acid marker selected from the group of the resistant alleles of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, and/or SEQ ID No. 10, wherein said allele is associated with Ao resistance. In certain embodiments, the cultivated spinach plant obtained by any of these aforementioned methods can exhibit at least partial resistance to Ao or at least substantial resistance to Ao. In certain embodiments, the cultivated spinach plant obtained by any of these aforementioned methods can be a haploid spinach plant. In certain embodiments, the cultivated spinach plant obtained by any of the aforementioned methods and including at least one of the alleles can include at least one transgenic trait. In such embodiments, the transgenic trait can be an agronomic trait of interest. Similarly, this may be applied for identifying cultivated spinach plants that comprise alleles associated with Ao and Pfs resistance.

Next to white rust resistance, resistance to downy mildew is favored for cultivated spinach plants. Downy mildew disease is an economically important disease of spinach. The disease is caused by the fungus-like organism Pfs belonging to the phylum of Oomycota, like Ao. Several races of the downy mildew pathogen have been identified and recognized. The emergence of new races of Pfs makes this pathogen a major threat for spinach production globally and identifying new sources of resistance is therefore necessary. Downy mildew symptoms first appear as pale yellowish spots with a gray to purple downy growth on leaf undersurfaces. This downy growth is most apparent during wet and humid weather. Infections may be scattered or numerous, but individual lesions often coalesce. Severely infected plants are stunted or they die. Downy mildew can reduce both spinach yield and quality, and can be devastating to susceptible cultivars.

In one embodiment of the current disclosure, said cultivated spinach (Spinacia oleracea L.) plant is further resistant against downy mildew caused by the plant pathogen Pfs.

A "Pfs resistant plant" or "downy mildew resistant plant" or a plant having "Pfs resistance" or a "Pfs resistant phenotype" refers to a spinach plant which is resistant against one or more pathogenic races (and pathogenic isolates) of Pfs, as determined in a qualitative resistance assay under controlled environmental conditions. In such a resistance assay, a plurality of plants (e.g., at least 2 replicates of at least 40 plants) of a genotype, are inoculated with a sporangial suspension of the race or isolate and incubated under suitable conditions. After a suitable incubation period (e.g., 7, 8, 9, 10, 11 or more days after inoculation), the plants are evaluated for symptoms. Susceptible controls should show sporulation at the time of symptom evaluation. Any plant showing sporulation on the cotyledons (and/or on the true leaf/leaves) is considered "susceptible", while any plant not showing any sporulation on the cotyledons (and/or on the true leaf/leaves) is considered "resistant". A plant genotype with more than 85%, preferably more than 90%, more preferably more than 95%, and most preferably 99% of the inoculated plants being classified as "resistant" plants is considered to be resistant against the race or isolate.

In a preferred embodiment, said resistance is provided by a fourth allele conferring resistance to Pfs, wherein said allele is located on chromosome 3, and wherein said allele co-segregates with at least one molecular marker selected from the group of the resistant alleles of SEQ ID No. 11, SEQ ID No. 12, and/or SEQ ID No. 13. Preferably, said fourth resistance allele co-segregates with at least two molecular markers selected from the group of the resistant alleles of SEQ ID No. 11, SEQ ID No. 12, and/or SEQ ID No. 13. More preferably, said fourth resistance allele co-segregates with the three resistant alleles of molecular markers SEQ ID No. 11, SEQ ID No. 12, and SEQ ID No. 13. In some embodiments, the Pfs resistance allele is present in the plant in homozygous state.

Said fourth resistance allele is closely linked with said third resistance allele, and vice versa, conferring resistance to Pfs and Ao respectively in the cultivated spinach plant. Said third and fourth resistance allele are both located on chromosome 3.

In some embodiments, the Ao, or Ao and Pfs resistant plant was produced by growing seed of inbred spinach variety designated as 'X17-003-104-8', representative sample of seed having been deposited under NCIMB Accession Number 43477.

Pathogen resistance is an important trait for cultivated spinach plants. In a preferred embodiment of the current disclosure, the cultivated spinach plant includes one or more other agronomic traits. Preferably, said agronomic traits are selected from the group of morphological traits, physiological traits, or sterility traits. Preferably, said agronomic traits are chosen from the group of bolting, plant height, leaf number, leaf erectness, leaf color, leaf type, and/or heat tolerance. Bolting is an important trait to consider when growing spinach in different seasons and regions. Plant height, leaf number and leaf erectness are important traits for machine harvesting. Leaf color and leaf type are important consumer traits. Cultivated spinach plants with resistance to Ao, or Ao and Pfs, and having one or more agronomic traits, enable an improved spinach production.

The present disclosure also provides seeds, cell or tissue material, progeny and/or propagation material derived from the cultivated spinach plant including the first, second, third and/or fourth resistance allele. Said seeds, cell or tissue material, progeny and/or propagation material are capable of growing into the cultivated spinach plant having resistance to Ao, or Ao and Pfs. Resistance to the specified plant pathogen may be visually assessed.

In one embodiment, assessment of resistance to Ao or Pfs comprises visual observation to determine the severity of the pathogen infection, using a resistance scoring system. The resistance scoring system is well known in the art.

In a preferred embodiment, the present disclosure provides cultivated spinach plants to be assayed for resistance or susceptibility to Ao, or Ao and Pfs, by any method to determine whether the cultivated spinach plant is very resistant, resistant, substantially resistant, mid-resistant, comparatively resistant, partially resistant, mid-susceptible, or susceptible. Phenotyping for Ao is based on visually screening plants to determine percentage of infected leaf area.

Preferably, the cultivated spinach plant shows a comparative resistance when compared to a non-resistant control cultivated spinach plant. Preferably, the non-resistant control cultivated spinach plant will be genetically similar except for the Ao, or Ao and Pfs, resistance allele or alleles in question. Such plants can be grown under similar conditions with equivalent or near equivalent exposure to the pathogen. In this aspect, the resistant plant or plants have less than 40%, 35%, 30%, 25%, 15%, 10%, 5%, 2%, 1%, 0.5%, or 0% of leaf area infected.

The percentage of leaf area infected is used to rate plants on a scale of 1 (susceptible) to 10 (resistant). Disease resistance is evaluated visually. The infection can be natural or from artificial inoculation. The score 10 is given for completely clean spinach leaves, hence spinach plant. The score 1 is given if the cultivated spinach plants are almost dead or completely wiped by the plant pathogen. Score two is better than score 1, and score 3 is worse than score 4. In the current disclosure, a threshold of six is defined to differentiate resistance (score ≥6) from susceptibility scores (score <5).

Preferably, the cultivated spinach plant including the first, second, and/or third resistance allele, conferring resistance to Ao, has a mean resistance score of 5, or preferably a mean resistance score of 6, 7, 8, or 9. Most preferably, the cultivated spinach plant including the first, second, and/or third resistance allele, conferring resistance to Ao, has a resistance score of 10.

Preferably, the cultivated spinach plant including the first, second, third, and/or fourth resistance allele, conferring resistance to Ao and Pfs, has a mean resistance score of 5, or preferably a mean resistance score of 6, 7, 8, or 9. Most preferably, the cultivated spinach plant including the first, second, third and/or fourth resistance allele, conferring resistance to Ao and Pfs, has a resistance score of 10.

In one embodiment, the whole genome of the cultivated spinach plant of current disclosure is transferred into a recipient spinach plant. This can be done by crossing the cultivated spinach plant to the recipient spinach plant to create a F1 spinach plant. The F1 spinach plant can be further selfed and selected for one, two, three, four, or more generations to produce Ao, or Ao and Pfs resistant plants. Selection pressure can be via plant pathogen resistance test, molecular marker selection, agronomic traits phenotype selection, or a combination thereof.

In another embodiment, at least the resistance-conferring parts of the cultivated spinach plant of current disclosure are transferred into the recipient spinach plant. This can be done by crossing the cultivated spinach plant to the recipient spinach plant to create the F1 spinach plant, followed by one or more backcrosses. The progeny resulting from the backcrosses can be further selfed to give new Ao, or Ao and Pfs resistant, spinach plants the desired elite agronomic traits.

In one embodiment, the recipient plant is an elite line having one or more certain agronomically important traits. As used herein, "agronomically important traits" include any phenotype in a plant or plant part that is useful or advantageous for human use. Examples of agronomically important traits include but are not limited to those that result in increased biomass production, increased food production, and improved food quality. Additional examples of agronomically important traits include pest resistance, vigor, development time (time to harvest), bolting tolerance, enhanced nutrient content, flavors or colors, salt, heat, drought and cold tolerance, and the like.

To select Ao, or Ao and Pfs, resistant spinach plants in the progeny plants, a resistant control plant and/or a susceptible control plant are involved. The population of the control plant is also challenged with the specified plant pathogen, under similar environmental conditions and pest or pathogen pressure. Resistance level of the progeny plant is compared to the resistance level of the control plant.

In one embodiment, the cultivated spinach plant of the current disclosure can be used to produce more spinach plants that are resistant to Ao, or Ao and Pfs, through plant breeding methods well known to those skilled in the art. The goal is to further develop new, unique and superior varieties and hybrids. Preferably, selection methods, e.g., molecular marker assisted selection, can be combined with breeding methods to accelerate the process. More preferably, the selection is combined with the molecular markers as disclosed in current disclosure.

In accordance with the disclosure, a novel spinach plant variety may be created by introgressing one or more resistance alleles against Ao, or Ao and Pfs into the genome of the cell or tissue material, seeds, progeny and/or propagation material of the cultivated spinach plant of current disclosure by molecular techniques. Preferably the one or more molecular markers, selected from the group of the resistant alleles of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, or SEQ ID No. 13, co-segregating with said resistance alleles, are introgressed into the genome of said cell or tissue material, seeds, progeny and/or propagation material. More preferably, multiple molecular markers co-segregating with said resistance alleles are introgressed into the genome of said cell or tissue material, seeds, progeny and/or propagation material.

The skilled person will readily understand that introgression is, however, not the sole manner in which the resistance allele can be introduced in the genome. Other methods may for instance involve the use of transgenic techniques, such as haploid cell fusion, plant transformation and the like. The introduction of said resistance allele may therefore also be performed by in vitro culture techniques, by protoplast fusion, by transformation or by a doubled haploid technique. Often, such techniques are not performed with intact plants but with cell or tissue material and/or propagation material of said plants.

In a preferred embodiment, the cell or tissue material or propagation material of the cultivated spinach plant of current disclosure are suitable for culturing.

It is reminded that a whole plant can be regenerated from a single plant cell, providing a transgenic plant or a part thereof. The regeneration can proceed by known methods. The seeds which grow by fertilization from this plant also contain this transgene in their genome.

In one embodiment, the method for generating the cultivated spinach plant of current disclosure, may, without limitation, be executed by using a tissue culture. Said tissue culture preferably includes cells, tissues or propagation material according to previous embodiments of the disclosure.

One embodiment of current disclosure also relates to a method for generating a cultivated spinach plant having resistance to Ao, wherein the method includes introgression of one or more resistance alleles conferring resistance to Ao, which co-segregate with one or more molecular markers, wherein said introgression includes the sequence of the resistant alleles of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, and/or SEQ ID No. 10 by using tissue culture.

Another embodiment of current disclosure relates to a method for generating a cultivated spinach plant having resistance to Ao and Pfs, wherein the method includes introgression of one or more resistance alleles conferring resistance to Ao and Pfs, which co-segregate with one or more molecular markers, wherein said introgression includes the sequence of the resistant alleles of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, and/or SEQ ID No. 13 by using tissue culture.

In one embodiment, the cells are regenerable cells derived from embryos, protoplasts, meristematic cells, callus, pollen, leaves, anthers, stems, petioles, roots, root tips, fruits, seeds, flowers, cotyledons, or hypocotyls.

Tissue cultured plants are clones; if the original mother plant used to produce the first explants is resistant to a pathogen or environmental condition, the entire crop would be resistant to the same problem, conversely any positive traits would remain within the line. Means for preparing and maintaining plant tissue cultures, in particular spinach plant cultures are well known in the art. In particular, tissue culture of the cultivated spinach plant described herein relates to the culture of protoplasts, calli, or plant cells, that are isolated from, or present in, intact parts of the Ao resistant plants described herein. Furthermore, tissue culture may refer to the culture of protoplasts, calli, or plant cells, that are isolated from, or present in, intact parts of plants of one or more Ao resistant spinach plant and Ao resistant progeny thereof, including those produced by crosses or backcrosses. In yet another aspect, tissue culture of the spinach plants described herein relates to the culture of protoplasts, calli, or plant cells, that are isolated from, or present in, intact parts of the Ao resistant plants described herein.

In one embodiment of the current disclosure, seeds are obtained from inbred spinach variety designated as 'X17-003-104-8', representative sample of seed having been deposited under NCIMB Accession Number 43477. Another preferred embodiment of the current disclosure is seed of the cultivated spinach plant. The cultivated spinach plant of the current disclosure produces viable seeds. In a more preferred embodiment, the seed of the current disclosure is capable of growing into the cultivated spinach plant, wherein the progeny is resistant to Ao, or Ao and Pfs. Spinach plants grown from the germinated seeds, and the resultant plants thereof may be used for further selection and breeding.

The present disclosure also provides progeny obtained by growing the cultivated spinach plant of the current disclosure.

In one embodiment the progeny of the cultivated spinach retains one or more resistance alleles which confer resistance to white rust, or white rust and downy mildew.

Progeny can be produced through either natural or artificial process, sexually or asexually, e.g., by cutting, grafting apomixis, layering, division, budding, grafting or tissue culture, wherein said progeny retains the resistance alleles. Preferably, the progeny further retains the agronomic traits. Preferably, at least 5% of said progeny is resistant to Pfs and Ao. For example, about 5% to about 15%, about 16% to about 25%, about 26% to about 50%, or 51% to about 99%, or more of said progeny is resistant to Ao. For example about 5% to about 15%, about 16% to about 25%, about 26% to about 50%, or 51% to about 99%, or more of said progeny is resistant to Pfs and Ao.

In one embodiment, the propagating material, derived from the cultivated spinach, is selected from the group of stems, cuttings, petioles, hypocotyls, cotyledons, flowers, anthers, pollen, ovaries, roots, root tips, protoplasts, callus, microspores, stalks, ovules, shoots, seeds, embryos, embryo sacs, egg cells, cells, meristems, buds, or leaves, and said propagation material is capable of growing into the cultivated spinach plant of the current disclosure.

Further, propagation material or seeds of the cultivated spinach plant of the current disclosure, may be used for generating a cultivated spinach plant having resistance to Ao, or Ao and Pfs.

One embodiment of the current disclosure also relates to a method for generating a cultivated spinach plant having resistance to Ao, wherein the method includes introgression of one or more resistance alleles conferring resistance to Ao, which co-segregate with one or more molecular markers, wherein said introgression includes the sequence of the resistant alleles of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, and/or SEQ ID No. 10 by vegetative reproduction.

Another embodiment of the current disclosure relates to a method for generating a cultivated spinach plant having resistance to Ao and Pfs, wherein the method includes introgression of one or more resistance alleles conferring resistance to Ao and Pfs, which co-segregate with one or more molecular markers, wherein said introgression includes the sequence of the resistant alleles of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, and/or SEQ ID No. 13 by vegetative reproduction.

In a preferred embodiment of the current disclosure, the seeds deposited under accession number NCIMB 43477 and progeny thereof are used in generating a spinach plant including resistance to Ao, or Ao and Pfs.

In a more preferred embodiment of the current disclosure, the seeds, progeny, and propagating material according to current disclosure are used in generating the cultivated spinach including resistance to Ao, or Ao and Pfs.

In a further aspect of the current disclosure, one or more molecular markers selected from the group of the resistant alleles of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, and/or SEQ ID No. 10 are used for diagnostic selection of Ao resistance alleles in spinach (*Spinacia oleracea* L.) plants, for identifying the presence of Ao resistance alleles in a plant, for monitoring introgression of Ao resistance alleles in spinach (*Spinacia oleracea* L.) plants, and/or developing other markers co-segregating with Ao resistance alleles.

In another embodiment of the current disclosure, one or more molecular markers selected from the group of the resistant alleles of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, and/or SEQ ID No. 13 are used for diagnostic selection of Ao and Pfs resistance alleles in spinach (*Spinacia oleracea* L.) plants, for identifying the presence of Ao and Pfs resistance alleles in a plant, for monitoring introgression of Ao and Pfs resistance alleles in spinach (*Spinacia oleracea* L.) plants, and/or developing other markers co-segregating with Ao and Pfs resistance alleles.

Improving the resistance of cultivars via standard breeding approaches is quite difficult and labor-intensive. Molecular or genetic markers aid in the development of particular traits of interest, like resistance.

Molecular markers have proven to be of great value for increasing the speed, accuracy, and efficiency of plant breeding. Most traits of agronomic value, e.g., pest resistance, yield and the like, are difficult to measure, often requiring a full growth season and statistical analysis of field trial results. Interpretation of the data can be obscured or confused by environmental variables. Occasionally, it has been possible for breeders to make use of conventional markers such as flower color which could be readily followed through the breeding process. If the trait is linked closely enough to a conventional marker, the likelihood of recombination occurring between them is sufficiently low that the trait and the marker co-segregate throughout a series of crosses. The marker becomes, in effect, a surrogate for the trait itself. Having a wide selection of molecular markers available throughout the genetic map provides breeders the means to follow almost any desired trait through a series of crosses, by measuring the presence or absence of a marker linked to the resistance allele that trait. The primary obstacle is the initial step of identifying a linkage between a marker and a resistance allele affecting the desired trait.

More molecular markers can be developed by using the Ao, or Ao and Pfs resistant spinach plants with agronomic traits of the present disclosure. In general, as the genetic distance between a molecular marker and a gene of interest becomes shorter, the marker and the gene are more closely localized to each other, and more likely to be inherited simultaneously; thus such markers are more useful. Methods of developing molecular markers are well known to one of ordinary skill in the art. The marks can be bi-allelic dominant, bi-allelic co-dominant, and/or multi-allelic co-dominant. The types of molecular markers that can be developed include, but are not limited to, restriction fragment length polymorphisms (RFLPs), isozyme markers, allele specific hybridization (ASH), amplified variable sequences of plant genome, self-sustained sequence replication, simple sequence repeat (SSR), single base-pair change (single nucleotide polymorphism, SNP), random amplification of polymorphic DNA (RAPDs), SSCPs (single stranded conformation polymorphisms); amplified fragment length polymorphisms (AFLPs) and microsatellites DNA. RAPD methods generally refer to methods of detecting DNA polymorphisms using differences in the length of DNAs amplified using appropriate primers. AFLP methods are essentially a combination of the above RFLP and RAPD methods, and refer to methods of selectively amplifying DNA restriction fragments using PCR to detect differences in their length, or their presence or absence.

One skilled in the art would be able to design primers for PCR detection of the molecular markers or methods other than PCR to detect said molecular makers (e.g., polymorphism detection methods such as nucleic acid sequencing and TILLING arrays).

The SNP markers of the current disclosure provide breeders with a tool in spinach molecular breeding to select spinach resistance to Ao or Ao and Pfs through, for instance, marker-assisted selected (MAS).

Enumerated Embodiments

The following enumerated embodiments are representative of some aspects of the disclosure.

1. A cultivated spinach (*Spinacia oleracea* L.) plant, wherein said plant is resistant to white rust caused by the plant pathogen *Albugo occidentalis*, characterized in that said resistance is provided by one or more alleles conferring resistance to said plant pathogen, and wherein said alleles co-segregate with at least one molecular marker selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, and/or SEQ ID No. 10.

2. Cultivated spinach (*Spinacia oleracea* L.) plant according to claim 1, characterized in that said resistance is provided by a first resistance allele located on chromosome 1 of said plant and wherein said allele co-segregates with at least one molecular marker selected from the group consisting of SEQ ID No. 1, SEQ ID No. 2, and/or SEQ ID No. 3.

3. Cultivated spinach (*Spinacia oleracea* L.) plant according to claim 1 or 2, characterized in that said resistance is provided by a second resistance allele located on chromosome 2 of said plant, wherein said allele co-segregates with at least one molecular marker selected from the group consisting of SEQ ID No. 4, SEQ ID No. 5, and/or SEQ ID No. 6.

4. Cultivated spinach (*Spinacia oleracea* L.) plant according to any one of the preceding claims 1-3, characterized in that said resistance locus is provided by a third resistance allele located on chromosome 3 of said plant and wherein said allele co-segregates with at least one molecular marker selected from the group consisting of SEQ ID No. 7, SEQ ID No. 8, SEQ ID No. 9, and/or SEQ ID No. 10.

5. Cultivated spinach (*Spinacia oleracea* L.) plant according any one of the preceding claims 1-4, characterized in that said plant is further resistant to downy mildew caused by the plant pathogen *Peronospora farinosa* f sp. *spinaciae*.

6. Cultivated spinach (*Spinacia oleracea* L.) plant according to claim 5, characterized in that said resistance is provided by a fourth allele conferring resistance to *Peronospora farinosa* f sp. *spinaciae*, characterized in that said allele is located on chromosome 3 and wherein said allele co-segregates with at least one molecular marker selected from the group consisting of SEQ ID No. 11, SEQ ID No. 12, and/or SEQ ID No. 13.

7. Cultivated spinach (*Spinacia oleracea* L.) plant according to claim 5 or 6, characterized in that said resistance to *Peronospora farinosa* f sp. *spinaciae* is to at least races 1 to 15 and race 17.

8. Cultivated spinach (*Spinacia oleracea* L.) plant according to any one of the preceding claims 1-7, characterized in that seeds obtained from said plant are representative for said plant, wherein the seeds are deposited under accession number NCIMBXXXXX.

9. Cell or tissue from a cultivated spinach (*Spinacia oleracea* L.) plant according to any one of the preceding claims 1-8, and said cell and tissue are suitable for culturing.

10. Seed of a cultivated spinach (*Spinacia oleracea* L.) plant according to any one of the preceding claims 1-8.

11. Seed capable of growing into a cultivated spinach (*Spinacia oleracea* L.) plant according to any one of the preceding claims 1-8.

12. Progeny of a cultivated spinach (*Spinacia oleracea* L.) plant according to any one of the preceding claims 1-8, wherein said progeny retains the resistance allele which confers resistance to white rust, or white rust and downy mildew.

13. Propagating material derived from a cultivated spinach (*Spinacia oleracea* L.) plant according to any one of the claims 1-8, wherein the material is selected from the group consisting of stems, cuttings, petioles, hypocotyls, cotyledons, flowers, anthers, pollen, ovaries, roots, root tips, protoplasts, callus, microspores, stalks, ovules, shoots, seeds, embryos, embryo sacs, egg cells, cells, meristems, buds, leaves, and said propagation material is capable of growing into a spinach (*Spinacia oleracea* L.) plant according to any one of the claims 1-8.

14. Use of seeds deposited under accession number NCIMBXXXXX and progeny thereof in generating a spinach plant comprising resistance to *Albugo occidentalis*, or *Albugo occidentalis* and *Peronospora farinosa* f sp. *spinaciae*.

15. Use of seeds according to claim 10 or 1, progeny according to 12, and propagating material according to claim 13 in generating a spinach plant comprising resistance to *Albugo occidentalis* or *Albugo occidentalis* and *Peronospora farinosa* f sp. *spinaciae*.

16. Use of one or more molecular markers selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, and/or SEQ ID No. 10 for diagnostic selection of *Albugo occidentalis* resistance alleles in spinach (*Spinacia oleracea* L.) plants, for identifying the presence of *Albugo occidentalis* resistance alleles in a plant, for monitoring introgression of *Albugo occidentalis* resistance alleles in spinach (*Spinacia oleracea* L.) plants, and/or developing other markers co-segregating with *Albugo occidentalis* resistance alleles.

17. Use of one or more molecular markers selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, and/or SEQ ID No. 13 for diagnostic selection of *Albugo occidentalis* and/or*Peronosporafarinosa* f sp. *spinaciae* resistance alleles in spinach (*Spinacia oleracea* L.) plants, for identifying the presence of *Albugo occidentalis* and/or *Peronospora farinosa* f. sp. *spinaciae* resistance alleles in a plant, for monitoring introgression of *Albugo occidentalis* and/or *Peronospora farinosa* f. sp. *spinaciae* resistance alleles in spinach (*Spinacia oleracea* L.) plants, and/or developing other markers co-segregating with *Albugo occidentalis* and/or *Peronospora farinosa* f. sp. *spinaciae* resistance alleles.

Further Embodiments
Breeding Methods

In a further embodiment, the spinach plant is an inbred line, especially an inbred line which can be used as a parent for F1 hybrid seed production. In another embodiment, the spinach plant is a hybrid, especially an F1 hybrid. An F1 hybrid may be generated by crossing a first inbred parent line which includes at least one of the resistance alleles, preferably in homozygous form, with a second inbred parent line. The first inbred parent line may be a line developed from using seeds deposited under NCIMB 43477 or from progeny of plants grown from these seeds, whereby the progeny retain the Ao, or Ao and Pfs resistance phenotype and the resistance allele (s).

The second inbred parent line may be any spinach line, i.e. it may completely lack Ao or Pfs resistance, it may include a different Ao or Pfs resistance gene (and different resistance phenotype), or it may also include at least one of the resistance alleles according to the current disclosure.

The resistance can be introduced into any other spinach plant by introgression from a plant grown from seeds of which a representative sample was deposited under NCIMB 43477, or any spinach plant derived therefrom and including at least one of the resistance alleles. The deposited seeds are therefore a source of the resistance of the disclosure, as are spinach plants not directly obtained from the deposit, but for example indirectly obtained (e.g., later released commercial varieties), which contain at least one of the resistance alleles.

A spinach plant including resistance against Ao, or Ao and Pfs, can be generated by the steps of: (a) providing a spinach plant including resistance against Ao, or Ao and Pfs; (b) crossing said spinach plant with another spinach plant to produce F1 seeds; (c) optionally selfing the plants grown from F1 seeds one or more times to produce F2, F3 or further generation selfing progeny; (d) identifying (or selecting) spinach plants grown from F1, F2, F3 or further generation selfing progeny which have resistance against Ao, or Ao and Pfs; (e) optionally crossing said identified (or selected) F1 progeny or selfing progeny to the spinach plant of step (b), to produce a backcross progeny; (f) optionally selecting backcross progeny including resistance against Ao, or Ao and Pfs.

The resistance alleles obtainable from (obtained from; as found in) plants deposited under NCIMB 43477, or progeny thereof, can be combined with other resistance genes or resistance loci or with other traits, such resistance against bacteria (e.g., *Pseudomonas syringae* pv. *spinacea; Erwinia carotovora*), fungi (e.g., *Colletotrichum dematium* f sp. *spinaciae; Stemphylium botryosum* f sp. *spinaciae*), viruses (e.g., viruses causing curly top disease) or nematodes. This can be done by traditional breeding techniques, e.g., by backcrossing in order to introduce one or more traits into a plant of the disclosure or in order to introduce the at least one of the alleles of a plant of the disclosure into another spinach plant including such one or more additional traits. Thus, in one aspect a plant of the invention is used as a donor of the resistance according to the current invention, while in another aspect a plant of the invention is used as recipient of one or more other traits.

The resistance alleles described in the current disclosure may be transferred to progeny by further breeding. In one aspect, progeny are F1 progeny obtained by crossing a plant of the disclosure with another plant or S1 progeny obtained by selfing a plant of the invention. Also encompassed are F2 progeny obtained by selfing the F1 plants, or further generation progeny. "Further breeding" encompasses traditional breeding techniques (e.g., selfing, crossing, backcrossing), marker-assisted breeding, and/or mutation breeding. In one embodiment, the progeny have the Ao, or Ao and Pfs resistance phenotype of plant of the current disclosure.

Haploid plants and/or double haploid plants of plant of the current disclosure are encompassed herein, which include resistance against Ao, or Ao and Pfs, as conferred by the alleles described in the current disclosure. Haploid and double haploid (DH) plants can for example be produced by anther or microspore culture and regeneration into a whole plant. For DH production, chromosome doubling may be induced using known methods, such as colchicine treatment or the like. So, in one aspect a spinach plant is provided, including Ao, or Ao and Pfs resistance phenotype as described, wherein the plant is a double haploid plant.

Additional Methods to Identify Resistance Alleles

Molecular markers may also be used to aid in the identification of the plants (or plant parts or nucleic acids obtained therefrom) containing the resistance gene or locus or allele(s). For example, one can develop one or more suitable molecular markers which are closely genetically (and preferably also physically) linked to the resistance gene, locus or allele. This can be done by crossing a resistant spinach plant with a susceptible spinach plant and developing a segregating population (e.g., F2 or backcross population) from that cross. The segregating population can then be phenotyped for Ao, or Ao and Pfs resistance and genotyped using, e.g., molecular markers such as SNPs (Single Nucleotide Polymorphisms), AFLPs (Amplified Fragment Length Polymorphisms; see, e.g., EP534858), or others, and by software analysis molecular markers which co-segregate with the Ao, or Ao and Pfs, resistance trait in the segregating population can be identified and their order and genetic distance (centimorgan distance, cM) to the resistance gene or locus can be identified. Molecular markers which are closely linked to resistance locus or loci, e.g., markers at a 5 cM distance or less, can then be used in detecting and/or selecting plants (e.g., plants of the invention or progeny of a plant of the invention) or plant parts including or retaining the introgression fragment including the resistance gene or locus. Such closely linked molecular markers can replace phenotypic selection (or be used in addition to phenotypic selection) in breeding programs, i.e. in Marker Assisted Selection (MAS). Preferably flanking markers are used in MAS, i.e. one marker on either side of the resistance gene or locus/loci. Similarly, the SNPs in this disclosure can be used to identify further molecular markers using the methods described above.

Allelism tests can also be used to determine whether the resistance allele in a spinach plant is the same allele or a different allele as the resistance allele as present in NCIMB 43477, or in progeny thereof. For instance, NCIMB 43477, or progeny thereof can be crossed with another spinach plant including the same resistance phenotype and in progeny of such a cross one can determine in which ratios the phenotype segregates. Allelism tests for dominant genes are known in the art (see, e.g., Hibberd et al., 1987, Phytopathology 77:1304-1307).

Any other type of molecular marker and/or other assay that is able to identify the relative presence or absence of alleles of interest in a plant or plant part can also be useful for breeding purposes, for diagnostic selection of Ao and/or Pfs resistance alleles in spinach plants, for identifying the presence of Ao and/or Pfs resistance alleles in a plant, for monitoring introgression of Ao and/or Pfs resistance alleles in spinach plants, and/or developing other markers co-segregating with Ao and/or Pfs resistance alleles.

EXAMPLES

The present disclosure is further exemplified by the following examples. The following examples are offered to illustrate, but not to limit the present disclosure. Methods according to the present disclosure may be realized in many different ways without departing from the scope of the disclosure.

Example 1: Resistance of the Cultivated Spinach Plants of Current Disclosure

Because white rust infection is dependent on the environmental conditions during the growing season, white rust field-resistance was evaluated in the winter of both 2014-2015 and 2016-2017 in Crystal City (Texas, US). Seeds of hundreds of genotypes were sown in three plots of 300 seeds each per genotype. After natural infection, resistance scores were estimated in discrete classes from 1 to 10 depending on the percentage of abaxial leaf surfaces having white rust lesions. The score 10 was given for completely clean spinach leaves. The score of 1 was given if the cultivated spinach plants were almost dead or completely affected by the plant pathogen. A threshold of 6 was defined to differentiate resistance (score ≥6) from susceptibility scores (score <5). Only the average score per genotype was available and used for statistical analysis.

The population of cultivated spinach (*Spinacea oleracea* L.) plants with resistance against Ao had a mean resistance score of 7.8. Seeds obtained from said spinach plants were used to grow new plants, and these new plants had a mean resistance score of 7.8. The mean resistance score of the control spinach plants, which had the same genetic background as the cultivated spinach plants but lacked the resistance alleles, was 1.8.

Example 2: Identification of Molecular Markers for Ao Resistance Alleles

Resistance to Ao is not a single gene resistance, but rather a polygenic and quantitative resistance. The genome of the Ao resistant spinach plants described in Example 1 was sequenced to ~56× on the ILLUMINA® HISEQ™ platform and mapped to the reference genome assembly "spinach_assembly-repeatdetect_PACBIO_V1.3" of spinach variety 'Viroflay' (SGSR, UC Davis Genome Center, Davis, USA) using SAMTOOLS (samtools.sourceforge.net). The reference genome assembly contained 2882 high quality contigs with an average length of 316.211,89 nucleotides. Variants were called and filtered in the GATK-package (gatk.broadinstitute.org). The candidate SNP were tested for co-segregation with Ao-resistance classes. Ten marker sequences that co-segregated with three resistance alleles for white rust in the cultivated spinach plants were identified.

Table 1 lists the sequences and SNPs of the ten Ao resistance markers. The Ao resistance marker sequences were each found to contain a SNP at nucleotide 101, which is marked in bold in the nucleotide sequence (second column from left). Ao resistance marker sequence SEQ ID No. 5 contained a second SNP at nucleotide 158, which is also marked in bold in the nucleotide sequence (second column from left). The nucleotide sequences shown in the table correspond to the susceptible alleles of the markers (second column from left). The SNP nucleotide changes are provided in the final two columns of the table. These SNP nucleotide changes were present in the Ao resistance markers (i.e., they are the resistant alleles of the markers), and only these sequences (i.e., the Ao resistance marker sequences that included the SNPs) were present in the Ao resistant plants. Further, the resistant plants were homozygous for the SNP resistance markers.

The location of the resistance alleles were mapped to the reference genome assembly "spinach_assembly-repeatdetect_PACBIO_V1.3" of spinach variety 'Viroflay'. The first Ao resistance allele was located on chromosome 1 and co-segregated with at least one molecular marker selected from the group of SEQ ID No. 1 including the T to C SNP at nucleotide 101, SEQ ID No. 2 including the T to A SNP at nucleotide 101, and/or SEQ ID No. 3 including the A to G SNP at nucleotide 101. The second Ao resistance allele was located on chromosome 2 and co-segregated with at least one molecular marker selected from the group of SEQ ID No. 4 including the G to A SNP at nucleotide 101, SEQ ID No. 5 including the T to C SNP at nucleotide 101 and the G to A SNP at nucleotide 158, and/or SEQ ID No. 6 including the C to A SNP at nucleotide 101. The third resistance allele was located on chromosome 3 and co-segregated with at least one molecular marker selected from the group of SEQ ID No. 7 including the G to T SNP at nucleotide 101, SEQ ID No. 8 including the C to T SNP at nucleotide 101, SEQ ID No. 9 including the C to T SNP at nucleotide 101, and/or SEQ ID No. 10 including the A to G SNP at nucleotide 101.

TABLE 1

| SEQ ID No. | Nucleotide sequence (5'-3') | SNP nucleotide at location 101 | SNP nucleotide at location 158 |
|---|---|---|---|
| SEQ ID No. 1 | AAGACAACTACCCTTTATAAATTACACTTGGGGATG TGGTTTCAACTCACCCTACGGTGGGCAGCAATGTCG AGGAGCTTGTCTACAAAAATATTCGATTTGAGGTTT GGGATTTGGGTGGGCAGGATAGACTGAGGACGTCAT GGACCACATATTATCGAGGAACACATGCTGTCATTG TGGTGATTGACAGCACAGATA | T to C | N/A |
| SEQ ID No. 2 | TGGGAAATATGGCATAATTCATGAATTTTTAACTTG CTTCGCTGAATGATCTGATCCTTGCTAAAAAATTCA ATCATGTTGGATTTTGGAAGAGGATGTTTTGAGTTG TAGCCCAAGGTGAACGAAGATTAAAAGCTTGTGTTC CTTAAACTACCTATGTGGAGAAAATTGTAACGAGTT CAATCGCTTCTTTTGGTTTAA | T to A | N/A |
| SEQ ID No. 3 | GTTGTAGCCCAAGGTGAACGAAGATTAAAAGCTTGT GTTCCTTAAACTACCTATGTGGAGAAAATTGTAACG AGTTCAATCGCTTCTTTTGGTTTAAATGATATTGTT GATATTGTGAGACTCCGTGAATTGGAGTGTTGTCGT ATGATCAAATATAGATTGGGTTACAACATTAGTCCT AATTGTATTAGGAAACCTAAT | A to G | N/A |
| SEQ ID No. 4 | CCTCGAAGTACCTCCCATGGCACGCTAGAAGTCAAC CAGGCCCGTCTGCAACCAGATCTCCATAGCCTCCTG CCAGCACGGATGGCTGCAAAAGCCTTCTGAAGCTCC GCCAAAGACCAGAAGGTGCGAAATGGCTCTCCGTC AGCCTACAGATGAACGAATCAGCTCAAAACCTATA CAAGTACAAAATACAAATTCAAA | G to A | N/A |
| SEQ ID No. 5 | TACGTGAAAACAATGCTGCGATTTTCGTATTTAAAC ATCTCCGCGCAGCCGTGTGTTCGCACGAAAGAAGTC GTGCGTTCGCACAAAACACCACTGAGTTTCTAATCC ATTATTGCAGATTTGTGTGGTCGCACGGGCAGAGCT GTGTGGTCGCACAGCAGTGTGCGCACACACGCTAA ATCTGTGTGGTCGCACAGCTA | T to C | G to A |

TABLE 1-continued

| SEQ ID No. | Nucleotide sequence (5'-3') | SNP nucleotide at location 101 | SNP nucleotide at location 158 |
|---|---|---|---|
| SEQ ID No. 6 | CAACTACACTAAACTAAAACTCTTTTTGAACTTTTCT TGATTTGATTTTCTCCTTTTTTTGTGTTTTAAATGAA TACTTTTCTCTATTTTTGGCTTTTTCACAAATTTACT TGCATCATTTATTCATTATATACAACATACTTCCCAA ACTTTGCCATTCAATCCAATAACAATCATTCCTCAAC TTTGCATAATCATTCA | C to A | N/A |
| SEQ ID No. 7 | GATATCCTGGTATTTTCAGTCTGACTGTTTGTATTAC TGTACTACTTCAATGATCAGTTCAATAGCTTATTGAC CCTCTTTTTTCCACCTGCTGATTGCTGTTCATCTGAT CATACTAATGTAACAGCTCAGCACAAAGCTATAGCCC GGAAGGTCTCCCAGCCAAAGCCTGTTCCTGGTGCTTT AGGGATTGACAGTAAC | G to T | N/A |
| SEQ ID No. 8 | ATCACAACAAGAACTTTGTGATACACTATGCAACTT AACTGCAGTTAGCACTTCAACGGGTATTTTATCTTG GTACCTTAGCATACAAAAGACAGTCAACCCTGTCGT TACCTTGTCTCAGCATCTCTTTTATTTTTGCAGGAT TGGGCGGAATGCATTTGGTGGTCTTTAGGGTTGAGG GAAATCACCGACTGCCACCCA | C to T | N/A |
| SEQ ID No. 9 | GCATGCAGGGTTTTGTTGACAATCTCGGGGAGGATG GATGCAGTATTAGTGTTGCCCTGGAGTCTCGACGTG GTGATGCCACCTTTTCAAAGCTCTTTGGCAAGCTTG TGCGAATTGATCGCATTCCTGGATTGGCTGACACAC GAACATATGAGGTAATTGAAAAGATAAATTGATTGG ATTTGGAAAGATGGATATGAG | C to T | N/A |
| SEQ ID No. 10 | GATGAATCTGTAGTTCTTTATTACTTGCATCTCTTT AATATTGCCATCCCTTGGGGGGAGGGTCTTATAGCA AGTAGTTTGTTCAAGAAACCTTATACTTAATAACCG GCGGCATCTAATCTAGATTTCACAATTTAAGGATGT TTTCTAGGTGACGGAAACTTTTATTGAGCATAATAG GCAGAAAGAAGTAGAAAACAG | A to G | N/A |

Example 3: Average Phenotypic Score for Different Genotypic Classes for White Rust Resistance To investigate whether combining the resistance alleles resulted in an elevated white rust resistance, the average resistance scores of the different resistance allele combinations were compared. The first (L1), second (L2) and third (L3) resistance alleles of current disclosure were tested in the comparison.

Table 2 gives an overview of the average phenotypic scores for the different genotypic classes for white rust resistance. For the three tests, different dosages of the resistance alleles were tested, including homozygous dosage (2), heterozygous dosage (1), or absent (0). Phenotypic average scores (APS) were phenotypic scores observed in the field trials. Scores of >6 were given to plants that showed partial resistance to Ao infection, and scores of <5 were given to plants that were susceptible to Ao infection. The % resistance scores (% R) were the percentage of the total number of plants found to be resistant (resistance score ≥6) for each of the categories (e.g., genotypic class).

TABLE 2

| Test I | | | |
|---|---|---|---|
| L1 dosage | L3 dosage | APS | % R |
| 2 | 2 | 8.1 | 100 |
| 0 | 2 | 5.7 | 67 |
| 1 | 2 | 5.3 | 50 |
| 1 | 1 | 5.1 | 38 |
| 2 | 1 | 5.3 | 33 |
| 2 | 0 | 5.0 | 0 |
| 0 | 1 | 3.9 | 0 |
| 1 | 0 | 1.0 | 0 |
| 0 | 0 | 3.6 | 0 |
| Test II | | | |
| L2 dosage | L3 dosage | APS | % R |
| 2 | 2 | 7.3 | 88 |
| 1 | 1 | 5.5 | 50 |
| 2 | 1 | 4.8 | 20 |
| 2 | 0 | 3.8 | 0 |
| 0 | 2 | 3.0 | 0 |
| 0 | 1 | 3.9 | 0 |
| 1 | 0 | 2.8 | 0 |
| 0 | 0 | 3.8 | 0 |
| 1 | 2 | n/a | 0 |
| Test III | | | |
| L1 dosage | L2 dosage | APS | % R |
| 2 | 2 | 7.4 | 81 |
| 1 | 1 | 5.5 | 50 |
| 1 | 2 | 4.8 | 38 |
| 0 | 2 | 4.3 | 17 |
| 0 | 1 | 2.8 | 0 |
| 1 | 0 | 3.0 | 0 |
| 0 | 0 | 3.8 | 0 |
| 2 | 1 | n/a | 0 |
| 2 | 0 | n/a | 0 |

As shown in Table 1, all genotypes that were homozygous for both L1 and L3 alleles were resistant towards white rust.

Combining L2 and L3 in homozygous dosage resulted in 88% of the genotypes being resistant. The presence of both L1 and L2 in homozygous dosage resulted in 81% of the genotypes being resistant. For the genotypes in which resistance alleles were not homozygously present, a significantly lower phenotypic average score (APS) as well as percentage of resistant genotypes (% R) was observed for all allelic combinations. Finally, the complete absence of any of the L1, L2, or L3 alleles resulted in all genotypes being susceptible.

Example 4: Identification of Molecular Markers for Pfs Resistance Alleles

Some of the Ao resistant spinach plants described in Example 1 were further resistant against downy mildew caused by the plant pathogen Pfs. The resistance to Pfs was to at least races 1-15 and race 17. The resistance to at least Pfs races 1-15 and race 17 was conferred by a fourth allele located on chromosome 3 and this allele co-segregated with at least one molecular marker selected from the group consisting of SEQ ID No. 11 including the A to G SNP at nucleotide 101, SEQ ID No. 12 including the G to A SNP at nucleotide 101, and/or SEQ ID No. 13 including the T to C SNP at nucleotide 101. The fourth resistance allele was closely linked with the third resistance allele, and vice versa, and conferred resistance to at least Pfs races 1-15 and race 17 and Ao respectively in the cultivated spinach plant. The third and fourth resistance allele were both located on chromosome 3.

Table 3 lists the sequence and SNP of the three Pfs resistance markers. The Pfs resistance marker sequences were each found to contain a SNP at nucleotide 101, which is marked in bold in the nucleotide sequence (middle column). The nucleotide sequences shown in the table correspond to the susceptible alleles of the markers (middle column). The SNP nucleotide changes are provided in the final column of the table. These SNP nucleotide changes were present in the Pfs resistance markers (i.e., they are the resistant alleles of the markers), and only these sequences (i.e., the Pfs resistance marker sequences that included the SNPs) were present in the Pfs resistant plants. The resistant plants were homozygous for the SNP resistance markers.

TABLE 3

| SEQ ID No. | Nucleotide Sequence (5'-3') | SNP nucleotide at location 101 |
|---|---|---|
| SEQ ID No. 11 | TGGTAAATTTCTCTGCATTT TCCTGCTGCTGAATGAATGA ATGCAGACAGCAGGATTTGT AGTTTTGTACCAATTTCAAA ATAATAATAATAATAATAAT AATGATGATGATGATGCTGT AATTTACTGTGTTTCACATA TTGAGAGTGATAGTTGTTCC CCTTGTTATTATGCATGCCA CAATTCCAATCATTTTATTG C | A to G |

TABLE 3-continued

| SEQ ID No. | Nucleotide Sequence (5'-3') | SNP nucleotide at location 101 |
|---|---|---|
| SEQ ID No. 12 | GTACTTCCTATTATCCACTT ACAAAAAGAAATAATAATCC CATTAACCGCAATATACTTA ATGCTAGCTCAAACATTGAA CCTATATAATCAGACTAATT GGCCTAAAAAAGATAATGTC GTACTGATTCAGTAGGTACT TTCTATTATCGACTTACAAA TAGAAATGACAAAATTAAGT TGAATCAACAACCAAATAAA T | G to A |
| SEQ ID No. 13 | AAAGACTATCCGAAATAGCC CAATTAGGAATTCTATATTA CGTGCCAATATTAACTTATA AAACCAAATAAAAATTAGAC AATTGTAGTAATTAACAAAT TACTTAATTATTACCTCCCT CTTTCCTTGAACTTTCCTCG AAATTTCTAAACCCTCCCAC CCACAACTTCCCCCTATAAA ATCACATCCCCTAATTATCT C | T to C |

A homozygous inbred spinach variety designated 'X17-003-104-8' was deposited with the NCIMB as described below. Inbred spinach variety 'X17-003-104-8' is resistant to both Ao and Pfs, as described above, and contains the first, second, third, and fourth resistance alleles. Inbred spinach variety 'X17-003-104-8' further contains the co-segregating Ao resistance markers SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, and SEQ ID No. 10, as well as the co-segregating Pfs resistance markers SEQ ID No. 11, SEQ ID No. 12, and SEQ ID No. 13.

DEPOSIT INFORMATION

At least 650 seeds of homozygous inbred spinach (*Spinacea oleracea* L.) variety 'X17-003-104-8' were deposited on Aug. 29, 2019 according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB number 43477. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

The invention claimed is:

1. A cultivated spinach (*Spinacia oleracea* L.) plant, wherein said plant is resistant to white rust caused by the plant pathogen *Albugo occidentalis* (Ao), wherein said resistance is provided by one or more resistance alleles conferring resistance to said plant pathogen, and wherein said alleles co-segregate with at least one molecular marker selected from the group of SEQ ID NO: 1 comprising a T to C SNP at nucleotide 101, SEQ ID NO: 2 comprising a T to A SNP at nucleotide 101, SEQ ID NO: 3 comprising an A to G SNP at nucleotide 101, SEQ ID NO: 4 comprising a G to A SNP at nucleotide 101, SEQ ID NO: 5 comprising a T to C SNP at nucleotide 101 and a G to A SNP at nucleotide 158, SEQ ID No. SEQ ID NO: 6 comprising a C to A SNP at nucleotide 101, SEQ ID NO: 7 comprising a G to T SNP at nucleotide 101, SEQ ID NO: 8 comprising a C to T SNP at nucleotide 101, SEQ ID NO: 9 comprising a C to T SNP at nucleotide 101, and SEQ ID NO: 10 comprising an A to G SNP at nucleotide 101.

2. The cultivated spinach plant of claim 1, wherein the Ao resistance is conferred by two or more resistance alleles comprising:
 (a) a first resistance allele located on chromosome 1, wherein said allele co-segregates with at least one molecular marker selected from the group of SEQ ID NO: 1 comprising the T to C SNP at nucleotide 101, SEQ ID NO: 2 comprising the T to A SNP at nucleotide 101, and SEQ ID NO: 3 comprising the A to G SNP at nucleotide 101;
 (b) a second resistance allele located on chromosome 2, wherein said allele co-segregates with at least one molecular marker selected from the group of SEQ ID NO: 4 comprising the G to A SNP at nucleotide 101, SEQ ID NO: 5 comprising the T to C SNP at nucleotide 101 and the G to A SNP at nucleotide 158, and SEQ ID NO: 6 comprising the C to A SNP at nucleotide 101; and
 (c) a third resistance allele located on chromosome 3, wherein said allele co-segregates with at least one molecular marker selected from the group of SEQ ID NO: 7 comprising the G to T SNP at nucleotide 101, SEQ ID NO: 8 comprising the C to T SNP at nucleotide 101, SEQ ID NO: 9 comprising the C to T SNP at nucleotide 101, and SEQ ID NO: 10 comprising the A to G SNP at nucleotide 101.

3. The cultivated spinach plant of claim 2, wherein the first resistance allele, the second resistance allele, and the third resistance allele are present in the plant in homozygous state.

4. The cultivated spinach plant of claim 1, wherein said plant is further resistant to downy mildew caused by the plant pathogen *Peronospora farinosa* f sp. *spinaciae* (Pfs), wherein the resistance to Pfs is to at least Pfs races 1 to 15 and race 17, and wherein said resistance is provided by a fourth resistance allele conferring resistance to said plant pathogen.

5. The cultivated spinach plant of claim 4, wherein said fourth resistance allele is located on chromosome 3, and wherein said fourth resistance allele co-segregates with at least one molecular marker selected from the group of SEQ ID NO: 11 comprising an A to G SNP at nucleotide 101, SEQ ID NO: 12 comprising a G to A SNP at nucleotide 101, and SEQ ID NO: 13 comprising a T to C SNP at nucleotide 101.

6. The cultivated spinach plant of claim 5, wherein the fourth resistance allele is present in the plant in homozygous state.

7. A propagating material derived from the cultivated spinach plant of claim 1, wherein said propagating material is selected from the group of stems, cuttings, petioles, hypocotyls, cotyledons, flowers, anthers, pollen, ovaries, roots, root tips, protoplasts, callus, microspores, stalks, ovules, shoots, seeds, embryos, embryo sacs, egg cells, cells, meristems, buds, and leaves, and said propagating material is capable of growing into the cultivated spinach plant of claim 1.

8. A progeny plant of the cultivated spinach plant of claim 1, wherein said progeny plant retains the one or more resistance alleles which confer resistance to Ao.

9. A progeny plant of the cultivated spinach plant of claim 4, wherein said progeny plant retains the resistance alleles which confer resistance to Ao and Pfs.

10. A tissue culture comprising regenerable cells from the propagating material of claim 7.

11. A cultivated spinach plant regenerated from the tissue culture of claim 10, wherein said plant retains the one or more resistance alleles which confer resistance to Ao.

12. A tissue culture of the cultivated spinach plant of claim 4.

13. A cultivated spinach plant regenerated from the tissue culture of claim 12, wherein said plant retains one or more of the resistance alleles which confer resistance to Ao and Pfs.

14. A cultivated spinach plant according to claim 1, said plant produced by growing seed of inbred spinach variety designated as 'X17-003-104-8', representative sample of seed having been deposited under NCIMB Accession Number 43477.

15. The cultivated spinach plant according to claim 4, wherein the plant was produced by growing seed of inbred spinach variety designated as 'X17-003-104-8', representative sample of seed having been deposited under NCIMB Accession Number 43477.

16. The seed of inbred spinach variety designated as 'X17-003-104-8', representative sample of seed having been deposited under NCIMB Accession Number 43477.

17. A method of generating a cultivated spinach plant comprising resistance to Ao or Ao and Pfs, said method comprising the steps:
    (a) crossing the spinach plant produced by growing the seeds deposited under NCIMB Accession Number 43477 with itself or with a second spinach plant; and
    (b) selecting an F1 progeny plant comprising resistance to Ao or an F1 progeny plant comprising resistance to Ao and Pfs.

18. The method of claim 17, further comprising the steps:
    (c) crossing the F1 progeny plant with a second spinach plant to produce backcross progeny plants; and
    (d) selecting a backcross progeny plant comprising resistance to Ao or a backcross progeny plant comprising resistance to Ao and Pfs.

19. A method of identifying the resistant spinach plant of claim 1, said method comprising the identification of one or more molecular markers selected from the group of the resistance alleles of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

20. A method of identifying the resistant spinach plant of claim 5, said method comprising the identification of one or more molecular markers selected from the group of the resistance alleles of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

21. A spinach plant comprising the one or more molecular markers identified by the method of claim 19.

22. A spinach plant comprising the one or more molecular markers identified by the method of claim 20.

23. A propagating material derived from the cultivated spinach plant of claim 4, wherein said propagating material is selected from one or more of stems, cuttings, petioles, hypocotyls, cotyledons, flowers, anthers, pollen, ovaries, roots, root tips, protoplasts, callus, microspores, stalks, ovules, shoots, seeds, embryos, embryo sacs, egg cells, cells, meristems, buds, and leaves, and said propagating material is capable of growing into the cultivated spinach plant of claim 4.

24. A cell culture comprising regenerable cells from the propagating material of claim 23.

* * * * *

UNITED STATES PATENT AND TRADEMARK OFFICE
CERTIFICATE OF CORRECTION

PATENT NO. : 11,365,427 B2  
APPLICATION NO. : 17/061318  
DATED : June 21, 2022  
INVENTOR(S) : De Visser et al.

Page 1 of 1

It is certified that error appears in the above-identified patent and that said Letters Patent is hereby corrected as shown below:

In the Claims

Column 35, Claim 1, Line 38:
DELETE "SEQ ID No."
The line should read "158, SEQ ID NO: 6 comprising a C to A SNP"

Signed and Sealed this
Ninth Day of August, 2022

Katherine Kelly Vidal
*Director of the United States Patent and Trademark Office*

SEQUENCE LISTING

<160> NUMBER OF SEQ ID NOS: 13

<210> SEQ ID NO 1

```
<211> LENGTH: 201
<212> TYPE: DNA
<213> ORGANISM: Spinacea oleraceae L.
<220> FEATURE:
<221> NAME/KEY: variation
<222> LOCATION: (101)..(101)
<223> OTHER INFORMATION: T to C

<400> SEQUENCE: 1
aagacaacta ccctttataa attacacttg gggatgtggt ttcaactcac cctacggtgg      60
gcagcaatgt cgaggagctt gtctacaaaa atattcgatt tgaggtttgg gatttgggtg    120
ggcaggatag actgaggacg tcatggacca catattatcg aggaacacat gctgtcattg    180
tggtgattga cagcacagat a                                              201

<210> SEQ ID NO 2
<211> LENGTH: 201
<212> TYPE: DNA
<213> ORGANISM: Spinacea oleraceae L.
<220> FEATURE:
<221> NAME/KEY: variation
<222> LOCATION: (101)..(101)
<223> OTHER INFORMATION: T to A

<400> SEQUENCE: 2
tgggaaatat ggcataattc atgaattttt aacttgcttc gctgaatgat ctgatccttg     60
ctaaaaaatt caatcatgtt ggattttgga agaggatgtt ttgagttgta gcccaaggtg    120
aacgaagatt aaaagcttgt gttccttaaa ctacctatgt ggagaaaatt gtaacgagtt    180
caatcgcttc ttttggttta a                                              201

<210> SEQ ID NO 3
<211> LENGTH: 201
<212> TYPE: DNA
<213> ORGANISM: Spinacea oleraceae L.
<220> FEATURE:
<221> NAME/KEY: variation
<222> LOCATION: (101)..(101)
<223> OTHER INFORMATION: A to G

<400> SEQUENCE: 3
gttgtagccc aaggtgaacg aagattaaaa gcttgtgttc cttaaactac ctatgtggag     60
aaaattgtaa cgagttcaat cgcttctttt ggtttaaatg atattgttag atattgtgag    120
actccgtgaa ttggagtgtt gtcgttgatc aaatatagat tgggttacaa cattagtcct    180
aattgtatta ggaaacctaa t                                              201

<210> SEQ ID NO 4
<211> LENGTH: 201
<212> TYPE: DNA
<213> ORGANISM: Spinacea oleraceae L.
<220> FEATURE:
<221> NAME/KEY: variation
<222> LOCATION: (101)..(101)
<223> OTHER INFORMATION: G to A

<400> SEQUENCE: 4
cctcgaagta cctcccatgg cacgctagaa gtcaaccagg cccgtctgca accagatctc     60
catagcctcc tgccagcacg gatggctgca aaagccttct gaagctccgc caaagaccag    120
aaggtgcgaa atggctctcc gtcagcctac agatgaacga atcagctcaa aacctataca    180
agtacaaaat acaaattcaa a                                              201
```

-continued

```
<210> SEQ ID NO 5
<211> LENGTH: 200
<212> TYPE: DNA
<213> ORGANISM: Spinacea oleraceae L.
<220> FEATURE:
<221> NAME/KEY: variation
<222> LOCATION: (101)..(101)
<223> OTHER INFORMATION: T to C
<220> FEATURE:
<221> NAME/KEY: variation
<222> LOCATION: (158)..(158)
<223> OTHER INFORMATION: G to A

<400> SEQUENCE: 5
tacgtgaaaa caatgctgcg attttcgtat ttaaacatct ccgcgcagcc gtgtgttcgc      60
acgaaagaag tcgtgcgttc gcacaaaaca ccactgagtt tctaatccat tattgcagat     120
ttgtgtggtc gcacgggcag agctgtgtgg tcgcacagca gtgtgcgcac acacgctaaa    180
tctgtgtggt cgcacagcta                                                 200

<210> SEQ ID NO 6
<211> LENGTH: 201
<212> TYPE: DNA
<213> ORGANISM: Spinacea oleraceae L.
<220> FEATURE:
<221> NAME/KEY: variation
<222> LOCATION: (101)..(101)
<223> OTHER INFORMATION: C to A

<400> SEQUENCE: 6
caactacact aaactaaaac tcttttttgaa cttttcttga tttgattttc tcctttttt      60 gtgttttaaa tgaaactttt ctctatttt ggcttttca caaatttact ttgcatcatt      120
tattcattat atacaacata cttcccaaac tttgccattc aatccaataa caatcattcc    180
tcaactttgc ataatcattc a                                              201

<210> SEQ ID NO 7
<211> LENGTH: 201
<212> TYPE: DNA
<213> ORGANISM: Spinacea oleraceae L.
<220> FEATURE:
<221> NAME/KEY: variation
<222> LOCATION: (101)..(101)
<223> OTHER INFORMATION: G to T

<400> SEQUENCE: 7
gatatcctgg tattttcagt ctgactgttt gtattactgt actacttcaa tgatcagttc      60
aatagcttat tgaccctctt ttttccacct gctgattgct gttcatctga tcatactaat    120
gtaacagctc agcacaaagc tatagcccgg aaggtctccc agccaaagcc tgttcctggt    180
gctttaggga ttgacagtaa c                                              201

<210> SEQ ID NO 8
<211> LENGTH: 201
<212> TYPE: DNA
<213> ORGANISM: Spinacea oleraceae L.
<220> FEATURE:
<221> NAME/KEY: variation
<222> LOCATION: (101)..(101)
<223> OTHER INFORMATION: C to T

<400> SEQUENCE: 8
atcacaacaa gaactttgtg atacactatg caacttaact gcagttagca cttcaacggg      60
tattttatct tggtacctta gcatacaaaa gacagtcaac cctgtcgtta ccttgtctca    120
```

```
gcatctcttt tattttttgca ggattgggcg gaatgcattt ggtggtcttt agggttgagg    180
gaaatcaccg actgccaccc a                                              201
```

```
<210> SEQ ID NO 9
<211> LENGTH: 201
<212> TYPE: DNA
<213> ORGANISM: Spinacea oleraceae L.
<220> FEATURE:
<221> NAME/KEY: variation
<222> LOCATION: (101)..(101)
<223> OTHER INFORMATION: C to T

<400> SEQUENCE: 9
```

```
gcatgcaggg ttttgttgac aatctcgggg aggatggatg cagtattagt gttgccctgg    60
agtctcgacg tggtgatgcc accttttcaa agctctttgg caagcttgtg cgaattgatc    120
gcattcctgg attggctgac acacgaacat atgaggtaat tgaaaagata aattgattgg    180
atttggaaag atggatatga g                                              201
```

```
<210> SEQ ID NO 10
<211> LENGTH: 201
<212> TYPE: DNA
<213> ORGANISM: Spinacea oleraceae L.
<220> FEATURE:
<221> NAME/KEY: variation
<222> LOCATION: (101)..(101)
<223> OTHER INFORMATION: A to G

<400> SEQUENCE: 10
```

```
gatgaatctg tagttcttta ttacttgcat ctctttaata ttgccatccc ttgggggggag   60 ggtcttatag caagtagttt gttcaagaaa ccttatactt aataaccggc ggcatctaat    120
ctagatttca caatttaagg atgttttcta ggtgacggaa acttttattg agcataatag    180
gcagaaagaa gtagaaaaca g                                              201
```

```
<210> SEQ ID NO 11
<211> LENGTH: 201
<212> TYPE: DNA
<213> ORGANISM: Spinacea oleraceae L.
<220> FEATURE:
<221> NAME/KEY: variation
<222> LOCATION: (101)..(101)
<223> OTHER INFORMATION: A to G

<400> SEQUENCE: 11
```

```
tggtaaattt ctctgcattt tcctgctgct gaatgaatga atgcagacag caggatttgt    60
agttttgtac caatttcaaa ataataataa taataataat aatgatgatg atgatgctgt    120
aatttactgt gtttcacata ttgagagtga tagttgttcc ccttgttatt atgcatgcca    180
caattccaat cattttattg c                                              201
```

```
<210> SEQ ID NO 12
<211> LENGTH: 201
<212> TYPE: DNA
<213> ORGANISM: Spinacea oleraceae L.
<220> FEATURE:
<221> NAME/KEY: variation
<222> LOCATION: (101)..(101)
<223> OTHER INFORMATION: G to A

<400> SEQUENCE: 12
```

```
gtacttccta ttatccactt acaaaaagaa ataataatcc cattaaccgc aatatactta    60
atgctagctc aaacattgaa cctatataat cagactaatt ggcctaaaaa agataatgtc    120
```

```
gtactgattc agtaggtact ttctattatc gacttacaaa tagaaatgac aaaattaagt        180
tgaatcaaca accaaataaa t                                                  201

<210> SEQ ID NO 13
<211> LENGTH: 201
<212> TYPE: DNA
<213> ORGANISM: Spinacea oleraceae L.
<220> FEATURE:
<221> NAME/KEY: variation
<222> LOCATION: (101)..(101)
<223> OTHER INFORMATION: T to C

<400> SEQUENCE: 13
aaagactatc cgaaatagcc caattaggaa ttctatatta cgtgccaata ttaacttata         60
aaaccaaata aaaattagac aattgtagta attaacaaat tacttaatta ttacctccct        120
tcttccttga actttcctcg aaatttctaa accctcccac ccacaacttc ccctataaa         180 atcacatccc ctaattatct c                                                  201
```